United States Patent
Kretschmer

(10) Patent No.: US 7,227,632 B2
(45) Date of Patent: Jun. 5, 2007

(54) ASSEMBLY FOR THE OPTICAL ILLUMINATION OF A PLURALITY OF SAMPLES

(75) Inventor: Hans-Richard Kretschmer, Berlin (DE)

(73) Assignee: Siemens Aktiengesellschaft, Munich (DE)

( * ) Notice: Subject to any disclaimer, the term of this patent is extended or adjusted under 35 U.S.C. 154(b) by 397 days.

(21) Appl. No.: 10/497,905

(22) PCT Filed: Dec. 4, 2002

(86) PCT No.: PCT/DE02/04491

§ 371 (c)(1),
(2), (4) Date: Jun. 7, 2004

(87) PCT Pub. No.: WO03/050315

PCT Pub. Date: Jun. 19, 2003

(65) Prior Publication Data

US 2005/0043632 A1      Feb. 24, 2005

(30) Foreign Application Priority Data

Dec. 5, 2001  (DE) .............................. 101 60 987

(51) Int. Cl.
   *G01N 21/01*   (2006.01)
(52) U.S. Cl. ........................... 356/244; 435/5
(58) Field of Classification Search ............... 356/244, 356/246, 432–440, 306, 318; 422/82.01, 422/82.11; 435/5, 6
See application file for complete search history.

(56) References Cited

U.S. PATENT DOCUMENTS

| 4,659,429 | A | | 4/1987 | Isaacson et al. |
| 4,802,951 | A | * | 2/1989 | Clark et al. .................... 216/56 |
| 5,696,629 | A | | 12/1997 | Berger et al. |
| 5,908,303 | A | | 6/1999 | Chung |

(Continued)

FOREIGN PATENT DOCUMENTS

DE              43 198 413        12/1994

(Continued)

OTHER PUBLICATIONS

V Lehmann, Porous Silicon—A New Material for Mems, Siemens AG Dept. ZFET ME 1, 81730 Munchen, Germany.

(Continued)

*Primary Examiner*—Hoa Q. Pham
(74) *Attorney, Agent, or Firm*—Young & Thompson

(57) ABSTRACT

An assembly for an optical read out device for biochips, in which in a manner known per se an optical path of light that is emitted from the samples is evaluated by a CCD camera. For this purpose, the samples are illuminated by a light source, which e.g. stimulates fluorescence in the samples. According to the invention, the light source consists of luminescent, porous silicon. The latter can constitute the surface of a luminous disc, which extends parallel to an analysis plane that is formed by the sample carrier. This allows the light source to be directly connected to the sample carrier, obviating the need for complex optical systems for distributing the light evenly from a punctiform or linear light source to the samples. The light source is particularly cost-effective and the required light intensity is low. The luminous disc can be simply produced by the etching of a silicon substrate.

7 Claims, 2 Drawing Sheets

U.S. PATENT DOCUMENTS

| | | | |
|---|---|---|---|
| 6,052,238 A * | 4/2000 | Ebbesen et al. | 359/738 |
| 6,248,539 B1 | 6/2001 | Ghadiri et al. | |
| 6,265,823 B1 | 7/2001 | Dobson et al. | |
| 6,534,011 B1 | 3/2003 | Karthe et al. | |
| 6,603,553 B1 | 8/2003 | Engelhardt | |
| 6,621,575 B1 | 9/2003 | Beuthan et al. | |

FOREIGN PATENT DOCUMENTS

| | | |
|---|---|---|
| DE | 196 51 772 | 7/1997 |
| DE | 197 25 050 | 12/1998 |
| DE | 199 40 752 | 4/2000 |
| DE | 198 58 490 | 6/2000 |
| DE | 199 16 749 | 10/2000 |
| DE | 199 30 607 | 1/2001 |
| DE | 199 37 797 | 3/2001 |
| DE | 100 24 132 | 8/2001 |
| DE | 100 17 824 | 10/2001 |
| DE | 199 29 875 | 10/2002 |
| WO | WO 00/58715 | 10/2000 |

OTHER PUBLICATIONS

Patent Abstracts of Japan, Chikage Doumoto, Light-Emitting Apparatus, Application No.: 09206894, Applicant Kyocera Corp.

* cited by examiner

ASSEMBLY FOR THE OPTICAL ILLUMINATION OF A PLURALITY OF SAMPLES

CROSS REFERENCE TO RELATED APPLICATIONS

This is the 35 USC 371 National Stage of International Application PCT/DE02/04491 filed on 4 Dec. 2002, which designated the United States of America

FIELD OF THE INVENTION

The invention relates to an assembly for the simultaneous optical illumination of a multiplicity of samples by means of a light source which consists of luminescent porous silicon.

BACKGROUND OF THE INVENTION

Such an assembly is known, for example, from German Patent Application DE 198 58 490 A1 (U.S. Pat. No. 6,621,575 corresponds). That document describes an assembly for the simultaneous optical illumination of a multiplicity of biological cells, each forming samples, by means of a light source made of luminescent porous silicon. This luminescent porous silicon is part of a luminous disk referred to as a nanosource array, which has a biocompatible adhesion layer for fixing the cells. The nanosource array is formed by a multiplicity of so-called apertures in the luminous disk, which are partially filled with the luminescent porous silicon. In this case, the luminescent porous silicon forms a surface with the rest of the luminous disk, so that it is directly next to the biocompatible adhesion layer.

A similar assembly for the illumination of samples is known, for example, from German Patent Application DE 199 40 752 A1. According to FIG. 4 of that document, this assembly consists of a sample support, for example a biochip, and a so-called system module which contains all of the components needed for illumination onto or through an array of samples arranged on the sample support. The assembly may be connected to another system module for optical analysis of the measurement signals output by the sample support.

The former system module for generating the light field has a matrix arrangement of light sources which, for example, may be formed by a microlaser array or a microdiode array. The effect achieved by interconnecting this multiplicity of microlight sources is that a luminous matrix with luminous points of uniform intensity can be produced on the sample support in order to optically analyze the individual samples.

SUMMARY OF THE INVENTION

It is an object of the invention to provide an assembly for the uniform optical illumination of sample arrays, in which the sample array can be accommodated on a comparatively small area.

According to the invention, particles for accumulating the samples' constituents provided with fluorescent labels are immobilized on the luminescent porous silicon. The particles for accumulating the constituents of the sample may consist of proteins, relatively small molecules, nucleic acids or their constituents, i.e. oligonucleotides. The effect of the immobilization process is that these particles are firmly connected to the sample support with a view to subsequently binding the samples' constituents to be detected per se.

Owing to its spongy structure, the porous silicon which is used as a light source is particularly well-suited for immobilization of the particles. This can be explained by the fact that the spongy structure provides a large internal surface area for accumulation of the particles during the immobilization. Therefore, a large number of particles can be immobilized per unit area of the sample support, since the internal surface area of the porous silicon allows a high density of accumulated particles. This advantageously favors progressive miniaturization of the samples, since a sufficient amount of the samples' constituents to be detected can be accumulated on the immobilized particles in a very small space, so as to achieve the detection thresholds dictated by the sensitivity of the analysis device being used.

The samples' constituents to be detected may consist of molecules, proteins, nucleic acids or their constituents, i.e. oligonucleotides. The latter, for example, will be accumulated on suitable particles over the sample support. This process is referred to as hybridization. Merely for completeness, it may be pointed out in this context that the samples' constituents to be detected are provided with so-called fluorescent labels in order to be detected. These labels contain a substance which can be fluorescently excited by means of the light source. The fluorescence can be recorded by the optical analysis device, and therefore allows information to be obtained regarding the presence of particular constituents in the samples, which have been accumulated on the immobilized particles owing to their respective specific properties.

It is proposed that the light source consist of luminescent porous silicon. This porous silicon may advantageously be produced in a straightforward way by treating a substrate of n- or p-doped silicon with hydrofluoric acid (cf. V. Lehmann, Porous Silicon—A New Material For MEMS, presented at the "Proceedings of the IEEE Micro Electro Mechanical Systems Work Shop" in San Diego, Calif. 11-15 February 1996, published in the related program on pages 1 to 6). The porous silicon obtained in this way can be made to luminesce by applying an electrical voltage, and may thereby be used as a light source for the samples. This provides a light source that has an emission face, the structure of this light source being extraordinarily compact. The medium generating light in this light source, that is to say the porous silicon, may be produced in an extraordinarily straightforward way by an etching treatment, so that the fabrication costs can be advantageously reduced.

According to an advantageous refinement of the invention, the porous silicon forms the surface of a luminous disk. A light source is thus used which emits the light from one face, namely the surface of the luminous disk. The emission face emits light with a consistent intensity, so that the samples can be illuminated uniformly.

It is advantageous for the luminous disk to have luminous zones made of the luminescent porous silicon on its surface. Each luminous zone may be assigned just one sample, so that the potential for miniaturization of the light source can be exploited in a particularly advantageous way, since the luminous zones can be introduced into the surface of the silicon substrate with a maximal accuracy by etching with the use of appropriate covering masks. It is possible to utilize tried and tested techniques for this, such as those which are widely known for the production of printed circuit boards by etching. The production of individual luminous zones has the great advantage that they can each produce light for just one sample, while no light is produced between the samples. Any stray light that occurs can thereby be minimized. In turn, this has a positive effect on the signal-to-noise ratio during the measurement process, so that the measurement result can be established more reliably. In particular, the size of the samples can be further reduced by means of this, since the measurement signals obtained from them can be recorded with a lower intensity without compromising the reliability of the measurement result.

BRIEF DESCRIPTION OF THE DRAWINGS

Further details of the invention can be found in the drawing, in which.

DETAILED DESCRIPTION OF THE INVENTION

Figure 1:
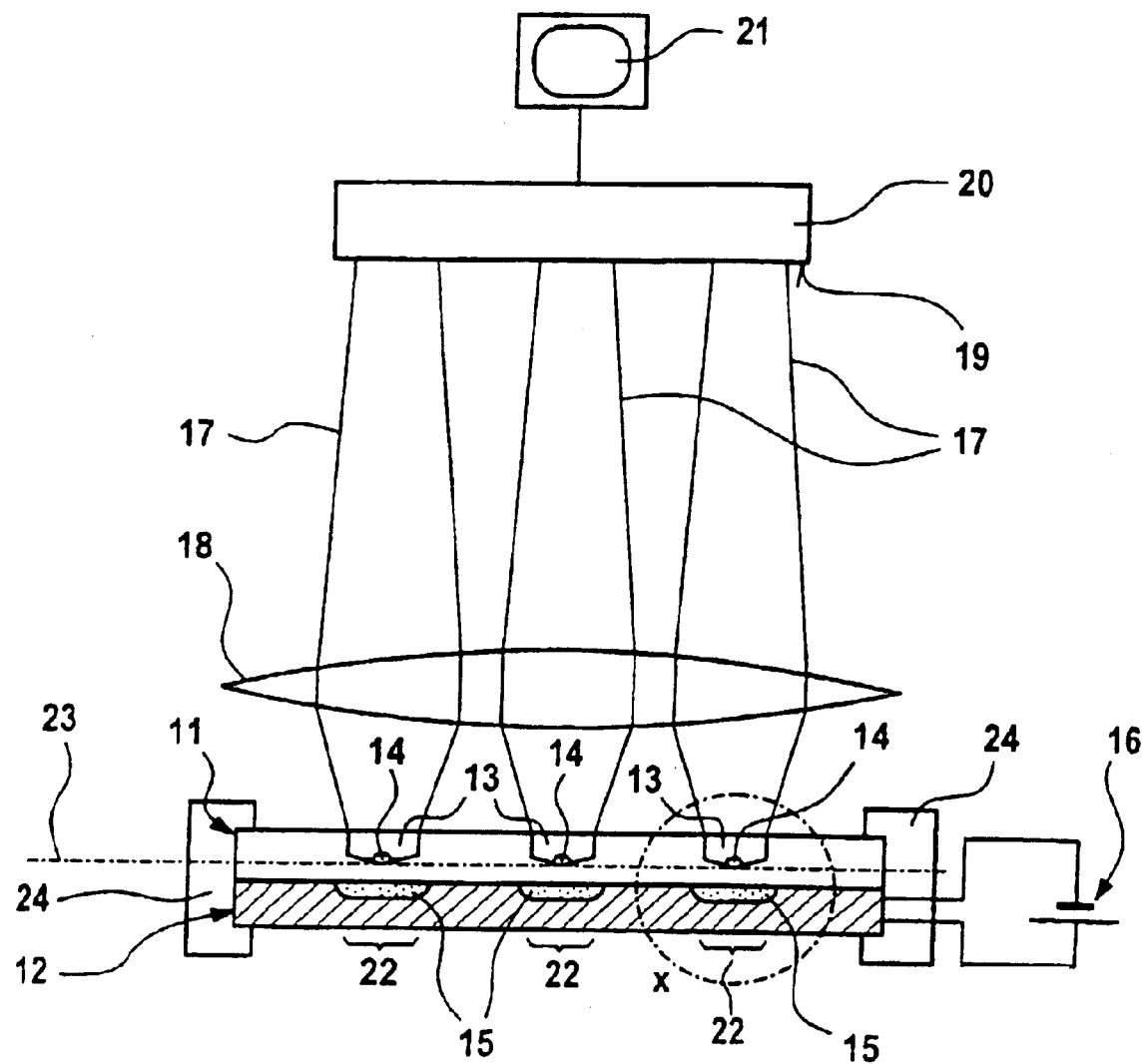
FIG. 1 generally shows a highly schematized device for the simultaneous optical analysis of a plurality of samples on a microtiter plate, with a light source made of luminescent porous silicon.

A device for the simultaneous optical analysis of samples according to FIG. 1 generally has a sample support, which is formed by a microtiter plate 11. The latter is connected to a luminous disk 12 which, for example, comprises porous silicon in order to illuminate wells 13 for holding samples 14 in the microtiter plate.

When the porous silicon 15 is made to luminesce by using a voltage supply 16, then a schematically indicated optical path 17 is created for each well, which starts from the porous silicon 15 and passes through the respective well 13 in the transparent microtiter plate, via optics 18 (indicated by a single converging lens in FIG. 1) onto a photosensitive face 19.

The photosensitive face 19 is part of a CCD camera 20 that produces an output signal for analysis of the measurement result, this signal being sent to a display screen 21 as the output device, for example.

The porous silicon 15 has an emission face 22 which is made up of a plurality of individual areas and is arranged parallel to the microtiter plate 11. The samples 14 are arranged two-dimensionally in an analysis plane 23 on the microtiter plate. This ensures that illumination is carried out with a uniform intensity through the samples 14, because they are at a uniform distance from the porous silicon 15, so that a reliable measurement result can be recorded by the CCD camera 20.

The microtiter plate 11 and the luminous disk 12 form an assembly which is held in the device by a schematically represented clamp 24. The clamp 24 makes it easy to interchange the assembly, the microtiter plate being connected to the luminous disk so that it can be released. In this way, it is possible to analyze different microtiter plates using the same luminous disk.

Figure 2:
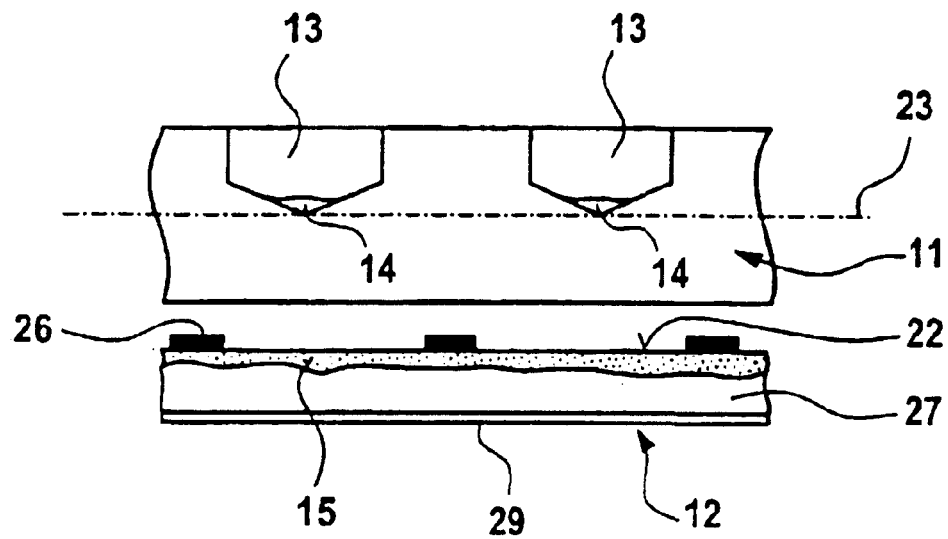
FIG. 2 shows the detail of a microtiter plate, through which illumination can be carried out by using a porous silicon light source.
Figure 3:
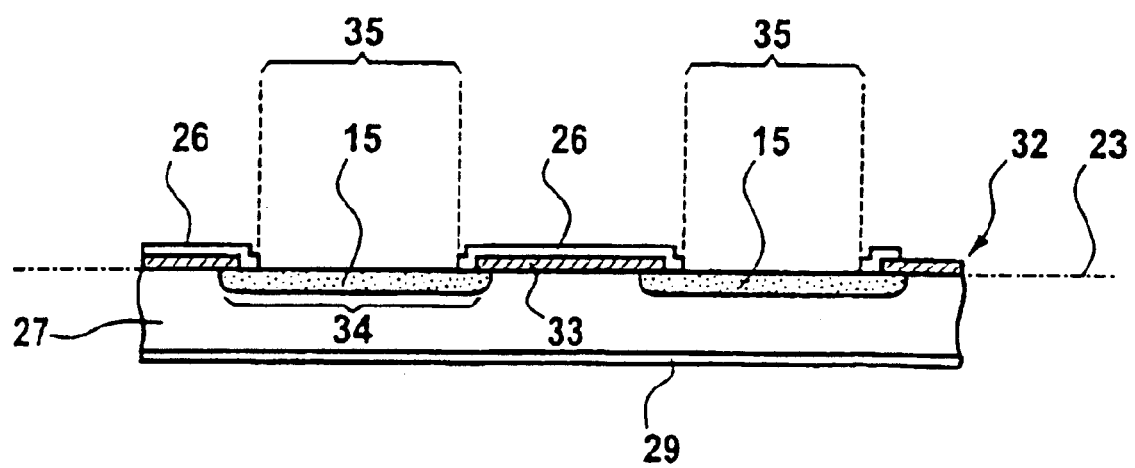
FIG. 3 shows an exemplary embodiment of the assembly according to the invention with a light source having luminous zones, which are formed by porous silicon and also constitute the sample support.

FIG. 1 represents an example of the structure of the device for illumination through the samples 14. Naturally, the assembly according to the invention may also be integrated in other known arrangements of such devices, for example those which are represented in FIGS. 2 and 3 of German Patent Application DE 199 40 752 A1. Accordingly, a semitransparent mirror at an angle of 45° to the optical path, for example, may be arranged in the optical path 17 between optics 18 and the photosensitive face 19 so that, by using a lateral arrangement of the luminous disk, the samples can be illuminated from the same direction as that in which the light is delivered for detection by the photosensitive face 19 (this arrangement is not represented in detail).

The following figures represent details of sample supports and light sources, the representations of which correspond to the detail X according to FIG. 1. Where the configurations according to FIGS. 1 to 3 comprise components of the same type, these will be denoted by the same reference numbers and will not be explained in further detail.

FIG. 2 represents an assembly in which the microtiter plate 11 is separate from the luminous disk 12. The porous silicon 15 of the luminous disk is provided with a network of interconnects 26, while a conductive layer 29 is applied to the opposite side of the luminous disk 12, which is formed by a silicon substrate 27. By connecting the conductive layer 29 and the interconnect 26 to a voltage source (not shown), the porous silicon 15 can be made to luminesce so that it provides illumination through the samples 14, starting from the emission face 22.

According to the invention, the luminous disk according to FIG. 2 may also be used in order to apply the samples directly onto the luminescent porous silicon (this is not represented). In this case, particles for accumulating the samples' constituents provided with fluorescent labels are immobilized directly on the surface of the luminous disk. This may be done in discrete regions, which will be referred to as spots. The sample constituents to be detected may, for example, be accumulated on the particles in the vicinity of these spots by a hybridization reaction.

FIG. 3 represents another exemplary embodiment, in which the light source formed by porous silicon 15 and the sample support are integrated in a single component. The sample support is designed as a biochip 32, with the silicon sustrate 27 forming the base. The electrically conducting layer 29 is located on the lower side, while the upper side is coated with an etch stop layer 33 that has holes in the vicinity of so-called spots 34. The silicon substrate 27 can therefore be converted into porous silicon 15 in the vicinity of these spots by means of an etching treatment. This creates luminous zones 35 in the vicinity of the spots, which together provide the luminous face of the biochip.

Oligonucleotides which are suitable for hybridization of the oligonucleotides to be detected in the sample, for example, may be immobilized on the spots (this is not represented in FIG. 3 owing to the size proportions).

The emission face 22 of the porous silicon therefore coincides with the sample plane 23 in this exemplary embodiment, so that particularly effective activation of fluorescent dyes in the sample's constituents to be detected can be carried out. The emission of light is furthermore restricted to the luminous zones 35 so that the occurrence of stray radiation can be minimized, since those regions on the sample support which are not occupied by the spots 34 remain dark.

In a similar way to that explained in connection with FIG. 2, the luminous zones are activated using the layer 29 and the interconnects 26, which surround the luminous zones 35 in a ring at their edge.

The invention claimed is:

1. An assembly for simultaneous optical illumination of a multiplicity of samples, the assembly comprising a light source of luminescent porous silicon, and particles for accumulating the samples' constituents having fluorescent labels, the particles being immobilized directly on the luminescent porous silicon.

2. The assembly as claimed in claim 1, wherein the porous silicon forms the surface of a luminous disk.

3. The assembly as claimed in claim 2, wherein the luminous disk has luminous zones made of the luminescent porous silicon on its surface.

4. The assembly as claimed in claim 1, wherein the luminescent porous silicon has a spongy structure that provides an internal surface area, and wherein the particles accumulate directly on the internal surface area.

5. An assembly for simultaneous optical illumination of a multiplicity of samples, the assembly comprising a substrate having plural luminous zones made of luminescent porous silicon, and particles for accumulating the samples' constituents having fluorescent labels, wherein the particles are immobilized on the luminescent porous silicon, and wherein each of the luminous zones has just one of the samples.

6. An assembly for simultaneous optical illumination of a multiplicity of samples, the assembly comprising:
   a light source of luminescent porous silicon having a spongy structure that provides an internal surface area; and
   particles adapted to accumulate the samples' constituents, said particles being immobilized on said internal surface area of said luminescent porous silicon.

7. The assembly as claimed in claim 6, further comprising a substrate having plural luminous zones made of said luminescent porous silicon, wherein each of said luminous zones has just one of the samples.

* * * * *